(12) United States Patent
Sarin et al.

(10) Patent No.: US 8,353,972 B2
(45) Date of Patent: Jan. 15, 2013

(54) SYNTHETIC FUEL AND METHOD OF PREPARATION THEREOF

(75) Inventors: Rakesh Sarin, Faridabad (IN); Ravindra Kumar, Faridabad (IN); Suresh Kumar Puri, Faridabad (IN); Anurag Ateet Gupta, Faridabad (IN); Ravinder Kumar Malhotra, Faridabad (IN); Satish Makhija, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 813 days.

(21) Appl. No.: 12/025,528

(22) Filed: Feb. 4, 2008

(65) Prior Publication Data

US 2009/0038211 A1   Feb. 12, 2009

(30) Foreign Application Priority Data

Aug. 10, 2007   (IN) .................. 1547/MUM/2007

(51) Int. Cl.
  *C10L 1/19*   (2006.01)
  *C10L 1/08*   (2006.01)
(52) U.S. Cl. ........................................ 44/388
(58) Field of Classification Search .............. 44/388, 44/437, 445, 443, 444
  See application file for complete search history.

(56) References Cited

U.S. PATENT DOCUMENTS

| | | |
|---|---|---|
| 3,381,022 A | 4/1968 | William |
| 5,004,478 A | 4/1991 | Vogel et al. |
| 5,681,800 A | 10/1997 | Duncan et al. |
| 5,689,031 A | 11/1997 | Berlowitz et al. |
| 6,274,029 B1 | 8/2001 | Wittenbrink et al. |
| 6,610,637 B2 | 8/2003 | Curtis et al. |
| 2004/0016174 A1* | 1/2004 | Connor et al. .................. 44/437 |

FOREIGN PATENT DOCUMENTS

| | | |
|---|---|---|
| EP | 1398364 | 3/2004 |
| WO | WO-9623855 | 8/1996 |
| WO | WO-2004009739 | 1/2004 |
| WO | WO-2004033513 | 4/2004 |
| WO | WO-2004106467 | 12/2004 |
| WO | WO-2004113474 | 12/2004 |
| WO | WO-2005001002 | 1/2005 |
| WO | WO-2006069407 | 6/2006 |

OTHER PUBLICATIONS

Baarschers et al. "Model compounds for biodegradation studies on hydrocarbon-type dielectric fluids". Canadian Journal Chemistry. 1983. 61(8). 1784-1787.*

* cited by examiner

*Primary Examiner* — Ellen McAvoy
*Assistant Examiner* — Latosha Hines
(74) *Attorney, Agent, or Firm* — Blank Rome LLP

(57) ABSTRACT

Disclosed is a novel synthetic fuel as alternative to diesel, wherein said synthetic fuel comprises branched esters and wherein the fuel having improved fuel properties such as zero aromatic, zero olefin, zero sulphur, low pour, high cetane diesel fuel with improved lubricity and oxidative stability. Further, the present invention provides a method of preparation of said esters.

15 Claims, No Drawings

SYNTHETIC FUEL AND METHOD OF PREPARATION THEREOF

FIELD OF THE INVENTION

This invention, in general, relates to a field of fuel. More particularly, the invention provides a novel synthetic diesel fuel having branched esters as an alternative to diesel with improved fuel properties and the method of preparation thereof.

BACKGROUND OF THE INVENTION

Mineral diesel is the main source of energy used worldwide and the most explored as a transportation fuel, however, it possess several disadvantages like; the sources of crude petroleum are limited and burning of diesel in engines causes the environmental hazardous problems. Moreover, diesel is a non-renewable source of energy. Additionally, availability of crude petroleum is confined to some areas of the world. Consequently, oil dependency of any nation on other nation poses a great threat for the security of oil deficient nations. Therefore, in order to circumvent these problems and to reduce the dependence on the fossil fuel, scientists have been prompted to look into alternate synthetic diesel fuel.

Last ten years have been focused on the benefits of producing cleaner, cost effective fuels process based on Fischer Tropsch technology that utilizes clean natural gas. Synthetic diesel finds applications in many diverse segments. The use of synthetic diesel in diesel engines results in substantial reduction of un-burnt hydrocarbons, carbon monoxide and particulate matters and is considered as a 'clean fuel'.

Unlike conventional diesel fuel which is produced as fractional distillate from petroleum, synthetic diesel is produced by Fischer-Tropsch process, wherein biomass, natural gas or coal is gasified to synthetic gas and subsequently liquified to produce synthetic diesel. Such processes are called Biomass-To-Liquids (BTL), Gas-to-Liquid (GTL) and Coal-to-Liquid (CTL) respectively. Such synthetic diesels are sometimes called FTD (Fischer-Tropsch diesel).

Synthetic diesel fuels are attractive because they are designed to provide both good engine performance and emission reductions. Use of synthetic diesel results in significant reductions in emissions, including NOx and particulate matter. Synthetic diesel fuels are characterized by excellent properties, such as very high cetane number and nil sulfur content. They can be used in existing diesel engines without modifications or mixed with petro-diesel. Synthetic diesels are even potentially suitable for aviation fuels with higher flashpoints.

DESCRIPTION OF PRIOR ARTS

The processes of preparation of upgraded synthetic diesel fuels have been treated as a serious scientific challenge. The prior art discloses many conventional methods for preparation of synthetic and other diesel fuels.

PCT Int. Application. No. 2006069407 to David et al. discloses the production of near zero aromatic diesel comprising the steps of catalytic conversion of Fisher-Tropic derived light olefins to distillates (COD) over a zeolite type catalyst at pressures of more than 50 bar, followed by one step of hydrotreating the COD product, wherein it involves hydrogenating both olefins and aromatics and finally collecting a hydrotreated fraction boiling between about 180° C. to 360° C. The cetane number is greater than 50 and total sulphur content of the fuel is 2 ppm. Low temperature operability is as low as −45° C. The fuel obtained contains 0.1% v/v aromatics and no detectable hydrocarbons.

PCT Int. Appl. No. 2005001002 discloses a highly paraffinic, moderately unsaturated distillate diesel or jet fuel blend stock and process thereof. The process comprises of the steps of converting syngas by a Fischer Tropsch process and further hydroprocessing the Fischer-Tropsch derived feedstock at a temperature of 525-775° F., a pressure of less than 1000 psig, and a liquid hourly space velocity of greater than 0.25 hr-1; and finally recovering a highly paraffinic, moderately unsaturated distillate fuel having cetane number greater than 60, wherein it comprises between 2 and 20 weight % unsaturates, which is less than 1 ppm sulfur, and peroxide precursors in an amount such that less than 5 ppm. The distillate fuel blend stock exhibits excellent combustion properties in diesel and jet engines as a result of the high paraffin content.

PCT Int. Appl. No. 2004113474 to Miller et al. discloses a highly paraffinic, moderately aromatic distillate fuel blend stock and process of preparation thereof, wherein the process comprises converting syngas to a Fischer Tropsch derived feedstock by a Fischer Tropsch process, and hydroprocessing the same at a temperature of 525-775° F., a pressure of less than 1000 psig, and a liquid hourly space velocity of greater than 0.25 hour to produce a distillate fuel blend stock. This is followed by adding aromatic blend to produce a highly paraffinic, moderately aromatic distillate fuel blend stock containing between 2 and 20 weight % aromatics and 80 weight % or greater paraffins. The diesel or jet fuel obtained has cetane number greater than 60, sulphur and nitrogen less than 1 ppm and aromatics as less as 5 weight %.

PCT Int. Appl. No. 2004106467 to Johnson et al. discloses low pour point syncrude products like a low-pour-point diesel fuel and synthetic lubricating base oils having an initial boiling point above 120° C. and process of preparation thereof, wherein the process comprises from a Fischer-Tropsch plant which involves de-waxing the recovered $C_5$ plus hydrocarbon feedstock in a hydroisomerization zone by contacting the $C_5$ plus syncrude feedstock with a hydrogenation catalyst (e.g., Pt or Pd) supported on an intermediate-pore silicoaluminophosphate (SAPO) or zeolite catalyst, followed by hydrofinishing, The hydrofinished products product yields a $C_{1-4}$-hydrocarbon (fuel gas) fraction, naphtha, synthetic diesel, having a lowered pour point and a lubricating base oil fraction.

PCT Int. Appl. No. 2004033513 Krug et al. discloses a low toxicity Fischer-Tropsch fuels suitable for use in a diesel engine and method for preparation thereof. Fractions of the Fischer-Tropsch derived-fuel mitigate the toxic effects of the intermediate boiling fraction. Thus by increasing the proportion of the higher boiling fraction, especially that fraction boiling above about 750° F., the toxicity of the overall composition, is significantly reduced. The fraction boiling above 800° F. is particularly effective in reducing the toxicity of the overall composition. Fuel compositions of the present invention generally have 95 weight percent point of the boiling range distribution higher than the 95 weight percent point of the boiling range distribution of conventional diesel. Due to the unique properties of Fischer-Tropsch fuel compositions disclosed in the invention, the fuels of the said patent are suitable for use in diesel engines, characterized by a boiling range distribution wherein the 5 weight % point is at 570° F. and the 95 wt. % point is 680° F., a kinematic viscosity at 40° C. of <5.5 cSt and a cloud point of less than −18° C.

EP 1398364 to Jakkula et al. discloses a fuel composition for diesel engines. The fuel composition comprises 0.1-99% by weight of a component or a mixture of components produced from biological raw material originating from plants and/or animals and/or fish. The fuel composition comprises 0-20% of components containing oxygen. Both components are mixed with diesel components based on crude oil and/or fractions from Fischer-Tropsch process. The resulting blend contains a higher paraffinic and naphthenic content, higher cetane No., and lower aromatic hydrocarbon content than standard diesel fuel and soot and NOx emissions are reduced.

PCT Int. Appl. No. 2004009739 to Hoek et al. discloses process of preparation of microcrystalline waxes and high-cetane-value middle distillates from high-molecular-weight waxes from Fischer-Tropsch reaction by initial hydrocracking-hydroisomerization of the product waxes, followed by one or more distillation steps to obtain a middle distillate fuel fraction and a microcrystalline wax having an initial boiling point of between 500 and 600° C. After de-oiling the wax additional de-oiling step is done to obtain a wax having oil content of between 0.1 and 2 weight %. The starting paraffin wax feedstock has a weight ratio of $C_{60}$ hydrocarbons to $C_{30-60}$ hydrocarbons in the ratio of 0.2:1 The product microcryst waxes have an initial boiling point 500-600° C., a congealing point of 95-120 and a penetration index (according to IP 376) at 43° C. of >0.8 mm. The byproduct middle distillates have a T 95 of 360° C., a cloud point of −20° C., a cold filter plugging point of −21° C., a d. of 0.78 kg/L, and a cetane index of 85. The Fischer-Tropsch middle distillates recovered have extremely good cold flow properties and have almost no impurities. Sulphur and nitrogen levels are below the detection limits, which are currently 5 ppm for sulphur and 1 ppm for nitrogen.

U.S. Pat. No. 6,274,029 to Wittenbrink, et al. discloses a distillate useful as a synthetic diesel fuel or as a diesel fuel blend stock material having a high cetane number and the process for preparing the distillate. The distillate is prepared from a Fischer-Tropsch wax, wherein a clean distillate useful as a fuel is heavier than gasoline and having a cetane number of at least about 60, preferably at least about 70, more preferably at least about 74, is produced, from a Fischer-Tropsch wax using Fischer-Tropsch catalyst, wherein the process also involves separating the waxy product into a heavier fraction and a lighter fraction. The nominal separation is at about 700° F., and the heavier fraction contains primarily 700° F.+ and the lighter fraction contains primarily 700° F. The distallate obtained has at least 95 weight % paraffin with an iso to normal ratio of about 0.3 to 3.0. The nitrogen and sulphur content of the fuel is less than or equal to 50 ppm.

U.S. Pat. No. 3,381,022 to William discloses esters or ester derivatives like acidic esters, diesters and mixtures thereof useful as additives in fuels, lubricating composition etc, wherein esters essentially comprises esters of substantially saturated polymerized olefin-substituted succinic acid and mono or polyhydric aliphatic alcohols or aromatic compounds like phenols and napthols having up to 40 carbon atoms. The esters are prepared by esterification, wherein ethylene glycol is reacted with substituted succinic anhydride or succinic acid or succinic acid halide.

U.S. Pat. No. 5,681,800 to Duncan et. al discloses a biodegradable synthetic base stock comprising the reaction product of a branched or linear alcohol and mixed acids and about 20 to 70 molar %, more preferably about 35 to 55 mole %, of at least one branched acid having a carbon number in the range between about $C_5$ to $C_{13}$, wherein the ester exhibits the following properties like at least 60% biodegradation, a pour point of less than −25° C., a viscosity of less than 7500 cps at 25° C. and oxidative stability of up to 45 minutes The biodegradable synthetic ester prepared from branched or linear alcohols can alternatively be blended with other, less biodegradable esters, wherein the blended product biodegrades better than either component alone.

U.S. Pat. No. 5,689,031 to Berlowitz, et al. discloses a distillate fuel heavier than gasoline like diesel, wherein same is prepared by a process comprising the steps of separating the waxy product of a Fischer-Tropsch process into a heavier fraction containing 700° F.+ and a lighter fraction containing 700° F.− and further separating the lighter fraction into at least two fractions wherein one fraction contains primary $C_{12}$-$C_{24}$ alcohols followed by hydroisomerizing and blending at least a portion of the recovered product. The distillate obtained has cetane No. of at least of 70 and contains at least 95 weight % paraffins. The content of sulphur and nitrogen is less than 50 ppm.

U.S. Pat. No. 6,610,637 to Curtis, et al is related a lubricant for use in diesel engine comprising synthetic base oil, viscosity modifier and detergent. Synthetic base oils can be selected from hydrocarbon oils, alkylene oxide polymers or esters of dicarboxylic acid and those made from $C_5$ to $C_{12}$ monocarboxylic acid and polyols and polyols ethers.

U.S. Pat. No. 6,458,176 to Yeh, et al. discloses a fuel composition for use in internal combustion engines comprising a major amount of a base fuel which contains no more than 10% by weight of olefins and no more than 10% by weight of esters e.g., the ortho esters of formic and acetic acid, ethers, glycols, polyoxyalkylene glycols, ethers and esters of glycerol, and carbonic acid esters., and greater than 5% by weight based on the total composition of an oxygenate selected from the group consisting of a saturated, aliphatic monohydric alcohol having on an average from 8 to 20 carbon atoms, one or more ketones having on an average 5 to 25 carbons, and mixtures of the alcohol(s) and ketone(s).

U.S. Pat. No. 5,004,478 to Vogel, et al. discloses a motor fuel for internal combustion engines containing a small amount of an additive comprising a conventional amino or amido containing detergent for cleaning, a base oil mixture and an ester of a monocarboxylic or polycarboxylic acid and an alkanol or polyol, The said ester is having a minimum viscosity of 2 $mm^2/s$ at 100° C. and the esters used are of aromatic di-, tri- and tetracarboxylic acids with long-chain aliphatic alcohols composed solely of carbon, hydrogen and oxygen, wherein the total number of carbon atoms of the esters is 22 or more and the molecular weight being from 370 to 1500, preferably from 414 to 1200. Preferable esters are adipates, phthalates, isophthalates, terephthalates and trimellitates of isooctanol, isononanol, isodecanol and isotridecanol and mixtures thereof.

PCT Int. Appl. No. 96/23855 discloses an additive composition comprising an ashless dispersant comprising an acylated nitrogen compound; and a carboxylic acid, or an ester of the carboxylic acid and an alcohol wherein the acid has from 2 to 50 carbon atoms and the alcohol has one or more carbon atoms provides an improvement in the lubricity of fuel oils and exhibits improved solubility in the fuel oil.

OBJECTS AND SUMMARY OF THE INVENTION

It is a principal object of the present invention to provide a novel synthetic fuel. It is further object of the present invention to provide this fuel as an alternate diesel fuel.

It is further object of the present invention to provide a novel synthetic fuel, wherein said fuel is characterized by having zero aromatic, zero olefin and zero sulphur content.

It is yet another object of the present invention to provide a novel synthetic fuel, wherein said fuel is characterized by having rich oxygen content and with improved low temperature properties like higher cetane number, improved lubricity and oxidation stability.

The above and other objects are attained in accordance with the present invention wherein there is provided following embodiments, however, the described embodiments hereinafter is in accordance with the best mode of practice and the invention is not restricted to the particular embodiments.

In accordance with another preferred embodiment of the present invention, there is provided a novel synthetic diesel fuel, wherein said fuel is chemically branched esters having a compound of formula I.

In accordance with other preferred embodiment of the present invention, there is provided a novel synthetic diesel fuel, wherein said fuel is chemically branched esters having beta branching.

In accordance with further embodiment of the present invention there is provided a novel synthetic diesel, wherein said fuel is chemically branched esters and wherein said ester is prepared by a process comprising dimerizing an alkyl alcohol, using Guerbet reaction to produce branched alcohol, oxidizing the resultant branched alcohols to obtain branched acids, esterifying the resultant branched acids (Guerbet acids) in the presence of acidic catalyst to produce branched esters, wherein the resultant ester is characterized by having improved diesel fuel properties.

In accordance with further embodiment of the present invention, the esters disclosed herein produced by the process as above, wherein the resultant ester is produced by esterification of branched acids in presence of alcohol and the acid catalyst so as to convert the regiospecific branched acid portion of the said acid into the esters, thereby the resultant esters provide excellent low temperature properties and oxidative stability of the synthetic diesel.

In accordance with yet another embodiment of the present invention there is provided a novel synthetic diesel, wherein, the resultant ester is capable of being used as 100% substitute of high speed diesel or as blend of 1-99% with conventional diesel or biodiesel.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The subject invention is aimed to find a diesel fuel with improved properties which is achieved by producing branched esters as fuels. The synthetic diesel comprising esters essentially has high cetane number, no suphur, no aromatics, no olefins, improved oxidative stability and excellent low temperature properties.

In an effort to find new alternative diesel fuel, an improved process for the production of biodiesel was developed (US Pat Appl. No. US 2006/0094890), which is basically an alkyl ester of fatty acids having the carbon numbers mainly from $C_{16-18}$. The use of biodiesel in conventional diesel engines results in substantial reduction of un-burnt hydrocarbons, carbon monoxide and particulate matters. Biodiesel is considered as a clean fuel as it has almost no sulphur, no aromatics and has about 10% built-in oxygen, which helps it to burn fully. Its higher Cetane number improves the ignition quality even in blends with petroleum diesel. However, some problems were encountered using straight chain fatty acids esters (biodiesel) like the poor low temperature properties and the poor oxidative stability. In the process of commercialization of biodiesel, it is very desirable, to improve the cold temperature properties and oxidative stability, so as to use this in more adverse conditions. There are many possible structural variations, which can impact upon the performance of esters. According to the present invention, it is disclosed that the presence of a specific beta branching in the fatty esters side of the molecule results in improved properties. Accordingly, the present invention provides a novel synthetic diesel fuel, which is chemically branched ester, rich in oxygen content and with improved low temperature properties, higher cetane number and improved oxidation stability.

The synthesis of synthetic diesel fuel can be achieved by any suitable process including chemical, biochemical, biological or biotechnological and is not restricted to a single process, wherein the prepared synthetic diesel is chemically branched ester, rich in oxygen content and with improved low temperature properties, higher cetane number and improved oxidation stability.

The esters according to present invention can be used as neat or in the blends with mineral diesel from 1 to 99% blends. This is fully mixable with diesel in any proportions. This branched fatty ester is prepared by the reaction of branched fatty acid with alcohol in the presence of acidic catalyst at the reflux temperature and is carried out at the temperature of 60-100° C.

Further, the esters according to the present invention for use as diesel fuel in compressed ignition engine is produced from a feedstock comprising of branched acids. Alternatively, it can be prepared starting from alcohols having carbon number from 3 to 16. These alcohols on dimererization using Guerbet reaction produce Guerbet alcohol (iso-alcohols), which on oxidation followed by esterification gave the desired esters. The following reaction scheme is further explained the steps involved in the process:

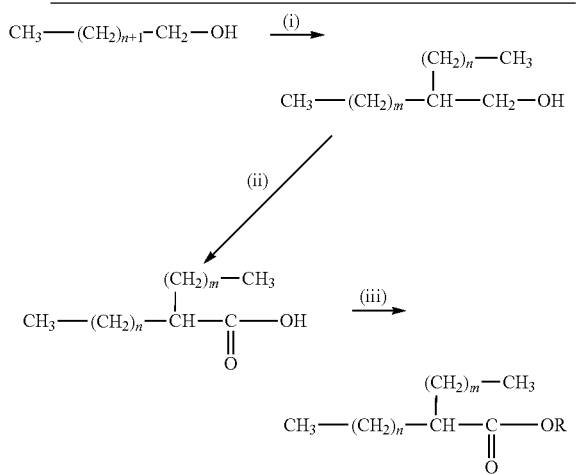

Scheme-1: Reagents and conditions: i) ZnO, KOH, CaO, Cu bronze, 230° C., 10 h, 80%; ii) Jones reagent, acetone, r.t., 6 h, 70%; iii) Alcohol, acid, reflux, 20 h, 75%.

The alcohols employed in the preparation of synthetic diesel comprising branched esters include the primary, secondary or tertiary like methanol, ethanol, propanol, iso-propanol, butanol, iso-butanol and tertiary butanol.

The acid catalyst employed in the preparation of synthetic diesel comprising branched esters includes sulfuric acid, p-toluenesulphonic acid, sulphated zircona, heterogeneous acid catalyst, zeolites and clay or their combinations. The quantities used of the catalyst are 0.1-5.0% by weight of the branched acid. Preferred catalyst quantities are from about 1-3% by weight.

Synthetic diesel comprising novel branched acids are specific beta-branched, i.e one hydrocarbon chain is connected to the beta position to the carboxylic group. Both of these hydrocarbon branches could be similar in length or different. Preferably, the carbon numbers of one chain is two carbons higher than the other chain.

The esterification reaction for preparation of novel esters for the synthesis of synthetic diesel can be carried out batch wise or continuously in any of the known reaction systems. In general, the alcohol is used in a 10% to 300% excess over the stoichiometric quantity required for the esterification reactions. The esterification reaction is carried out with substantially anhydrous alcohols. Suitable catalysts for esterification include any acid catalyst particularly sulfuric acid and p-toluenesulphonic acid.

The synthetic diesel fuel produced has s kinematic viscosity at 40° C. as measured by ASTM D445 (may be) below about 5.0 cSt but not lower than 2.0 cSt as measured at 40° C. The kinematic viscosity plays a role in the diesel fuel pump ability as well as the fuel injectors ability to efficiently inject fuel. High viscosity fuels negatively influence the fuel atomisation process limiting the formation fine droplets that lead to poor air fuel mixing within the combustion chamber (cylinder) resulting in turn in incomplete combustion accompanied by loss of power and economy. Excessively low viscosities lead to fuel pump leakage, incorrect metering and the inability for the fine atomised spray to penetrate the length of the combustion chamber and will result in poor combustion and in turn, result in loss of power and economy. A viscosity between 2.0 and 6.0 cSt as tested by ASTM D445 at 40° C. is preferred.

The synthetic diesel of the present invention comprises of branched esters which has improved cloud point. The cloud point is the temperature at which a cloud of wax crystals first appears in a fuel sample that is cooled under conditions described by ASTM D2500. The pour point is the lowest temperature at which movement of the fuel sample can be determined when the sample container is tilted to 45° angle. The apparatus used is the same as for the cloud point. The sample must be cooled following the procedure described in ASTM D97. The cold filter plugging point is determined as defined by International Petroleum Standard IP-309 and ASTM D 6371-99. It determines the lowest temperature where 20 ml of fuel can be drawn through a 45-micron screen in 60 seconds with 200 mm of water (1.96 kPa) of vacuum.

The synthetic diesel of the present invention comprising branched esters has also improved oxidation stability and the same was carried out using Rancimat equipment model 743 as described by EN-14112. The oxidation was induced by passing a stream of purified air at the rate of 10 L/Hr. through the biodiesel sample (approx. 5 ml), kept at constant temperature. The vapors released during the oxidation process, together with the air, are passed into the flask containing 60 ml of water which has been demineralized or distilled and contains an electrode for measuring the conductivity. The electrode is connected to a measuring and recording device. It indicates the end of the induction period when the conductivity begins to increase rapidly. This accelerated increase is caused by the dissociation of volatile carboxylic acids produced during the oxidation process and absorbed in the water. When the conductivity of this measuring solution is recorded continuously, an oxidation curve is obtained whose point of inflection is known as the induction; which provides the characteristic value for the oxidation stability. The limit as per the specification in this method is 6 hours minimum.

The synthetic fuel properties according to the present invention have shown better characteristics. The properties are evaluated in comparison with biodiesel and illustrated in Table I as following:

TABLE I

Fuel properties of synthetic fuel vis-a-vis biodiesel

| S. No. | Specifications (Unit) | Test method D 6751-07 | Biodiesel Limits | Methyl ester (C16) | Ethyl ester (C16) | Methyl ester (C24) |
|---|---|---|---|---|---|---|
| 1 | Cetane number, Min | D613 | 47 | 62.3 | 62.5 | 63.3 |
| 2 | Water and sediments, % vol, max | D2709 | 0.05 | nil | nil | nil |
| 3 | Cloud Point (° C.), Max | D2500 | Report | −39 | <−51 | 17 |
| 4 | Phosphorus Content, (% mass), Max | D4951 | 0.001 | nil | nil | nil |
| 5 | Sulphur, (% mass), Max | D5453 | 0.0015 | nil | nil | nil |
| 6 | Copper strip corrosion, (3 hrs @ 40° C.), Max | D130 | No. 3 | No. 1 | No. 1 | No. 1 |
| 7 | Distillation % v/v recovered @ (360° C.), Max | D1160 | 360 | 360 | 360 | 423 |
| 8 | Flash point, (° C.), Min. | D 93 | 130 | 60.8 | 64.0 | 71.0 |
| 9 | Methanol content, (% vol), max | EN14110 | 0.2 | nil | nil | nil |
| 10 | Na/K, (ppm), max | EN14538 | 5 | nil | nil | nil |
| 11 | Ca/Mn. (ppm) | EN14538 | 5 | nil | nil | nil |
| 12 | K. V. @ 40° C. (cSt) | D 445 | 1.9-6 | 4.32 | 4.14 | 9.79 |
| 13 | Acid number (mg KOH/gm), Max | D664 | 0.8 | 0.02 | 0.06 | 0.02 |
| 14 | CCR (% wt) of 100% Residue | D 4530 | 0.050 | 0.019 | 0.02 | 0.02 |
| 15 | Oxidn stability (Ind. time, hr), min | EN14112 | 3 h | >10 h | >9 | >7 h |
| 16 | Sulphated ash (% mass), max | D 874 | 0.02 | 0.01 | 0.01 | 0.01 |

TABLE I-continued

Fuel properties of synthetic fuel vis-a-vis biodiesel

| S. No. | Specifications (Unit) | Test method D 6751-07 | Biodiesel Limits | Fuel properties | | |
|---|---|---|---|---|---|---|
| | | | | Methyl ester (C16) | Ethyl ester (C16) | Methyl ester (C24) |
| 17 | Methanol content, (% vol), max | EN14110 | 0.2 | nil | nil | nil |
| 18 | Free glycerin, (% mass), max | D6584 | 0.020 | nil | nil | nil |
| 19 | Total glycerin (% mass), max | D6584 | 0.24 | nil | nil | nil |

Further, the synthetic fuel properties according to the present invention are evaluated in comparison with petroleum diesel, wherein said synthetic fuel is used as 10% blend with conventional diesel and the results are illustrated in Table II as following:

TABLE II

Fuel properties of synthetic fuel blends (10%) in diesel

| S. No. | Specifications (Unit) | Test method IS-1460 | Limits E-III | Fuel properties | | |
|---|---|---|---|---|---|---|
| | | | | Methyl ester (C16) (10% in diesel) | Ethyl ester (C16) (10% in diesel) | Methyl ester (C24) (10% in diesel) |
| 1 | Cetane Index, min | D4737 | 46 | 51.8 | 51.5 | 51.4 |
| 2 | Pour point (° C.), max | D5949 | 3 (W) 15 (S) | −6 | −6 | −6 |
| 3 | CFPP, (° C.), max | D6371 | 6 (W) 18 (S) | −2 | −3 | −3 |
| 4 | Total contaminant, (mg/kg) max | EN12662 | 24 | 20 | 18 | 16 |
| 5 | Cu corrosion, 3 hrs @ 100° C., max | ISO2160 | No. 1 | No. 1 | No. 1 | No. 1 |
| 6 | Distillation % v/v recovered 90% @ 360° C., Min. | ISO3405 | 95 | 97.0 | 92.0 | 90 |
| 7 | Flash point, (° C.), Min. | P: 20 | 35 | 57 | 54 | 53 |
| 8 | Water, (mg/kg), max | ISO6296 | 200 | nil | nil | nil |
| 9 | K. V. @ 40° C. (cSt) | ISO3104 | 2-4.5 | 3.23 | 3.30 | 3.44 |
| 10 | Density @ 15° C., (Kg/m$^3$) | D4052 | 820-845 | 843.2 | 844.0 | 842.7 |
| 11 | Acidity, total, (mg KOH/gm), Max | P: 2 | To report | 0.06 | nil | nil |
| 12 | Acidity, inorganic | P: 2 | nil | nil | nil | nil |
| 13 | CCR (% wt of 10% Residue), | ISO10370 | 0.30 | 0.20 | 0.10 | 0.10 |
| 14 | Sulphated ash (% mass), max | ISO6245 | 0.01 | <0.01 | <0.01 | <0.01 |
| 15 | Sulphur (% mass), max | D5433 | 350 | nil | nil | nil |
| 16 | Lubricity, wsd 1.4 @ 60° C., (μ), max | ISO12156-1 | 460 | 440 | 430 | 425 |
| 17 | PAH, (% mass), max | EN12916 | 11 | nil | nil | nil |
| 18 | Oxidation stability, g/m$^3$, max | D2274 | 25 | 16 | 18 | 10 |

Further, the synthetic fuel properties according to the present invention are evaluated in comparison with petroleum diesel and the results are illustrated in Table III as following:

TABLE III

Fuel properties of synthetic fuel vis-a-vis diesel

| S. No. | Specifications (Unit) | Test method IS-1460 | Limits Euro-III | Methyl ester (C16) | Ethyl ester (C16) | Methyl ester (C24) |
|---|---|---|---|---|---|---|
| 1 | Cetane Number, min | ISO5165 | 51 | 62.3 | 62.5 | 63.3 |
| 2 | Pour point (° C.), max | D5949 | 3 (W) 15 (S) | −51 | <−51 | 9 |
| 3 | CFPP, (° C.), max | D6371 | 6 (W) 18 (S) | <−34 | <−34 | 15 |
| 4 | Total contaminan, (mg/kg) max | EN12662 | 24 | nil | nil | nil |
| 5 | Cu corrosion, 3 hrs @ 100° C., max | ISO2160 | No. 1 | No. 1 | No. 1 | No. 1 |
| 6 | Distillation % v/v recovered 90% @ 360° C., Min. | ISO3405 | 95 | 360 | 360 | 423 |
| 7 | Flash point, (° C.), Min. | P: 20 | 35 | 60.8 | 64.0 | 71.0 |
| 8 | Water, (mg/kg), max | ISO6296 | 200 | nil | nil | nil |
| 9 | K. V. @ 40° C. (cSt) | ISO3104 | 2-4.5 | 4.32 | 4.14 | 9.79 |
| 10 | Density @ 15° C., (Kg/m$^3$) | D4052 | 820-845 | 862 | 856 | 855 |
| 11 | Acidity, total, (mg KOH/gm), Max | P: 2 | To report | 0.02 | 0.06 | 0.02 |
| 12 | Acidity, inorganic | P: 2 | nil | nil | nil | nil |
| 13 | CCR (% wt of 10% Residue), | ISO10370 | 0.30 | 0.019 | 0.02 | 0.02 |
| 14 | Sulphated ash (% mass), max | ISO6245 | 0.02 | 0.01 | 0.01 | 0.01 |
| 15 | Sulphur (% mass), max | D5433 | 350 | nil | nil | nil |
| 16 | Lubricity, wsd 1.4 @ 60° C., (μ) max | ISO12156-1 | 460 | 436 | 433 | 430 |
| 17 | PAH, (% mass), max | EN12916 | 11 | nil | nil | nil |
| 18 | Oxidation stability, g/m$^3$, max | D2274 | 25 | 15 | 14 | 21 |

Following examples further illustrate the present invention without limiting the scope of the invention.

EXAMPLE 1

The synthetic fuel was prepared by using a 1000 ml glass reactor, provided with thermostat, mechanical stirring, sampling outlet, and condensation system. Octanol-1 (300 g) was charged to the reactor and ZnO (2 g), KOH (6 g), CaO (5 g) and Cu Bronze (1.5 g) were added. The above reaction mixture was heated at 200° C. for 8 hours to complete the reaction. The reaction mixture was filtered and purified by distillation to get 2-hexyl-1-decanol (250 g). 2-Hexyl-1-decanol (250 g) was reacted with Jones reagent (200 ml) in acetone (200 ml) to get 2-hexyl-1-decanoic acid. 2-Hexyl-1-decanoic acid produced (200 g) was again charged to the above reactor and subsequently, methanol (200 g) and sulfuric acid (6.0 g) were added slowly to the reactor with stirring. The reaction mixture was refluxed till completion of the reaction. The reaction mixture was passed through basic alumina to get rid of residual catalyst. The catalyst free mixture was fractionated to separate un-reacted methanol and synthetic diesel. Prepared synthetic fuel was evaluated for fuel properties and results were tabulated.

EXAMPLE 2

To the reactor as in Example 1, decanol-1 (300 g) was charged to the reactor and ZnO (2 g), KOH (6 g), CaO (5 g) and Cu Bronze (1.5 g) were added. The above reaction mixture was heated at 200° C. for 6 h to complete the reaction. The reaction mixture was filtered and purified by distillation to get 2-octyl-1-dodecanol (250 g). 2-octyl-1-dodecanol (250 g) was reacted with Jones reagent (200 ml) in acetone (200 ml) to get 2-octyl-1-dodecanoic acid. 2-Octyl-1-dodecanoic acid (200 g) was again charged to the reactor and subsequently, methanol (200 g) and sulfuric acid (6.0 g) were added slowly to the reactor with stirring. The reaction mixture was refluxed till completion of the reaction. The reaction mixture was passed through basic alumina to get rid of residual catalyst. The catalyst free mixture was fractionated to separate un-reacted methanol and synthetic diesel. Prepared synthetic diesel was evaluated for fuel properties and results were tabulated.

EXAMPLE 3

2-Hexyl-1-decanoic acid (100 g) prepared as in Example-1, was reacted with ethanol (100 g) and p-toluenesulphonic acids (5 g) for reflux till the completion of the reaction. The reaction mixture was passed through basic alumina to get rid of residual catalyst. The catalyst free mixture was fractionated to separate un-reacted methanol and synthetic diesel. Prepared synthetic diesel was evaluated for fuel properties and results were tabulated.

EXAMPLE 4

2-Octyl-1-dodecanoic acid (100 g) prepared as in Example-2 was reacted with ethanol (100 g) and p-toluenesulphonic acids (5 g) for reflux till the completion of the reaction. The reaction mixture was passed through basic alumina to get rid of residual catalyst. The catalyst free mixture was fractionated to separate un-reacted methanol and synthetic diesel. The synthetic diesel prepared was evaluated for fuel properties and results were tabulated.

While this invention has been described in detail with reference to certain preferred embodiments, it should be appreciated that the present invention is not limited to those precise embodiments rather, in view of the present disclosure, which describes the current best mode for practicing the invention, many modifications and variations, would present themselves to those skilled in the art without departing from the scope and spirit of this invention.

We claim:

1. A fuel composition comprising
   (i) a compound of formula I:

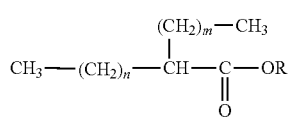

STR 1 wherein
   R is methyl, ethyl, propyl, iso-propyl, butyl, iso-butyl, tertiary-butyl or a mixture thereof;
   n is 3 to 16; and
   m is 3 to 16; and
   (ii) from about 1 to about 99% by weight of diesel or biodiesel;
wherein said fuel composition has a kinematic viscosity at 40° C. as measured by ASTM D445 of between about 2.0 and about 6.0.

2. The fuel composition according to claim 1, wherein m and n are the same.

3. The fuel composition according to claim 1, wherein the fuel composition is an alternate to diesel.

4. The fuel composition according to claim 1, wherein the fuel composition has a cetane number of at least 45.

5. The fuel composition according to claim 1, wherein the fuel composition is oxygen rich and has a high oxidative stability.

6. The fuel composition according to claim 1, wherein the fuel composition has a better low temperature property than diesel.

7. The fuel composition according to claim 1, wherein the fuel composition has a better combustion property than diesel.

8. The fuel composition according to claim 1, wherein the fuel composition has a zero sulphur content, zero aromatics content and zero olefin content.

9. The fuel composition according to claim 1, wherein said compound is a substitute for diesel.

10. The fuel composition according to claim 1, wherein said fuel composition comprises from about 1 to about 99% by weight diesel.

11. The fuel composition according to claim 1, wherein said fuel composition comprises from about 1 to about 99% by weight biodiesel.

12. The fuel composition according to claim 1, wherein m and n are different.

13. A fuel composition consisting of
    (i) a compound of formula I:

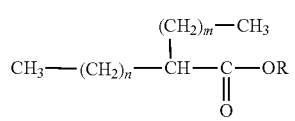

STR 1 wherein
   R is methyl, ethyl, propyl, iso-propyl, butyl, iso-butyl, tertiary-butyl or a mixture thereof;
   n is 3 to 16; and
   m is 3 to 16; and
   (ii) from about 1 to about 99% by weight of diesel or biodiesel;
wherein said composition has a kinematic viscosity at 40° C. as measured by ASTM D445 of between about 2.0 and about 6.0.

14. The fuel composition according to claim 13, wherein said fuel composition consists of a compound of Formula I and from about 1 to about 99% by weight diesel.

15. The fuel composition according to claim 13, wherein said fuel composition consists of a compound of Formula I and from about 1 to about 99% by weight biodiesel.

* * * * *